(12) United States Patent
Zones et al.

(10) Patent No.: US 7,622,032 B2
(45) Date of Patent: *Nov. 24, 2009

(54) HYDROCARBON CONVERSION USING MOLECULAR SIEVE SSZ-74

(75) Inventors: Stacey I. Zones, San Francisco, CA (US); Allen W. Burton, Jr., Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/614,683

(22) Filed: Dec. 21, 2006

(65) Prior Publication Data

US 2007/0144939 A1  Jun. 28, 2007

Related U.S. Application Data

(60) Provisional application No. 60/754,865, filed on Dec. 28, 2005.

(51) Int. Cl.
*C10G 47/16* (2006.01)
*C10G 35/06* (2006.01)
*C07C 5/02* (2006.01)
*C07C 5/22* (2006.01)
*C07C 2/66* (2006.01)
*C07C 2/52* (2006.01)
*C07C 1/00* (2006.01)

(52) U.S. Cl. .................. 208/27; 208/111.11; 208/138; 208/111.35; 208/120.01; 585/671; 585/739; 585/467; 585/475; 585/418; 585/481; 585/533; 585/357; 585/469; 585/639; 585/733; 585/943; 585/275

(58) Field of Classification Search ............... 208/27, 208/111.01, 111.35, 138, 739, 120.01; 585/671, 585/739, 467, 475, 418, 481, 533, 357, 469, 585/639, 733, 943, 275

See application file for complete search history.

(56) References Cited

U.S. PATENT DOCUMENTS

| | | | |
|---|---|---|---|
| 3,709,853 A | 1/1973 | Karapinka et al. | |
| 3,852,207 A | 12/1974 | Stangeland et al. | |
| 3,894,107 A | 7/1975 | Buffer et al. | |
| 3,904,513 A | 9/1975 | Fischer et al. | |
| 3,960,978 A | 6/1976 | Givens et al. | |
| 4,086,408 A | 4/1978 | Karol et al. | |
| 4,157,294 A | 6/1979 | Iwao et al. | |
| 4,181,598 A | 1/1980 | Gillespie et al. | |
| 4,347,121 A | 8/1982 | Mayer et al. | |
| 4,376,722 A | 3/1983 | Chester et al. | |
| 4,377,497 A | 3/1983 | Chester et al. | |
| 4,446,243 A | 5/1984 | Chester et al. | |
| 4,526,942 A | 7/1985 | Chester et al. | |
| 4,734,537 A | 3/1988 | Devries et al. | |
| 4,810,357 A | 3/1989 | Chester et al. | |
| 4,910,006 A | 3/1990 | Zones et al. | |
| 4,921,594 A | 5/1990 | Miller | |
| 4,939,311 A | 7/1990 | Washecheck et al. | |
| 4,962,261 A | 10/1990 | Abrevaya et al. | |
| 4,986,894 A * | 1/1991 | Keville et al. | 208/27 |
| 5,082,990 A | 1/1992 | Hsieh et al. | |
| 5,095,161 A | 3/1992 | Abrevaya et al. | |
| 5,105,044 A | 4/1992 | Han et al. | |
| 5,105,046 A | 4/1992 | Washecheck | |
| 5,149,421 A | 9/1992 | Miller | |
| 5,232,675 A * | 8/1993 | Shu et al. | 423/328.2 |
| 5,238,898 A | 8/1993 | Han et al. | |
| 5,316,753 A | 5/1994 | Nakagawa | |
| 5,321,185 A | 6/1994 | van der Vaart | |
| 5,336,825 A | 8/1994 | Choudhary et al. | |

OTHER PUBLICATIONS

U.S. Appl. No. 11/614,670, filed Dec. 21, 2006, entitled Molecular Sieve SSZ-74 Composition of Matter and Synthesis Thereof, 20 pages.
U.S. Appl. No. 11/614,688, filed Dec. 21, 2006, entitled Reduction of Oxides of Nitrogen in a Gas Stream Using Molecular Sieve SSZ-74, 18 pages.
U.S. Appl. No. 11/614,695, filed Dec. 21, 2006, entitled Partial Oxidation Using Molecular Sieve SSZ-74, 25 pages.
U.S. Appl. No. 11/614,701, filed Dec. 21, 2006, entitled Acylation Using Molecular Sieve SSZ-74, 18 pages.
U.S. Appl. No. 11/614,705, filed Dec. 21, 2006, entitled Oxygenate Conversion Using Molecular Sieve SSZ-74, 19 pages.
U.S. Appl. No. 11/614,638, filed Dec. 21, 2006, entitled Gas Separation Using Molecular Sieve SSZ-74, 17 pages.
U.S. Appl. No. 11/614,714, filed Dec. 21, 2006, entitled Synthesis of Amines Using Molecular Sieve SSZ-74, 18 pages.
U.S. Appl. No. 11/614,720, filed Dec. 21, 2006, entitled Treatment of Engine Exhaust Using Molecular Sieve SSZ-74, 25 pages.
U.S. Appl. No. 11/614,726, filed Dec. 21, 2006, entitled Beckmann Rearrangement Using Molecular Sieve SSZ-74, 22 pages.
Zones et al., Ordered silicon vacancies in the framework structure of the zeolite catalyst SSZ-74, Nature Materials, Aug. 2007, pp. 631-635, Macmillian Publishers Limited.
Koningsveld, Building scheme for MEL and MFI, Compendium of Zeolite Framework Types, 2007, Elsevier, 2007.
Koningsveld, Building scheme for SVR, Compendium of Zeolite Framework Types, 2007, Elsevier, 2007.
"News from the Structure Commission in 2008", http://www.iza-structure.org/, Sep. 18, 2008.

* cited by examiner

*Primary Examiner*—Thuan Dinh Dang
(74) *Attorney, Agent, or Firm*—Richard J. Sheridan

(57) ABSTRACT

The present invention relates to new crystalline molecular sieve SSZ-74 prepared using an hexamethylene-1,6-bis-(N-methyl-N-pyrrolidinium) dication as a structure-directing agent, and processes employing SSZ-74 in a catalyst.

61 Claims, 1 Drawing Sheet

US 7,622,032 B2

HYDROCARBON CONVERSION USING MOLECULAR SIEVE SSZ-74

This application claims the benefit under 35 USC 119 of Provisional Application No. 60/754,865, filed Dec. 28, 2005.

BACKGROUND OF THE INVENTION

1. Field of the Invention

The present invention relates to new crystalline molecular sieve SSZ-74, a method for preparing SSZ-74 using a hexamethylene-1,6-bis-(N-methyl-N-pyrrolidinium) dication as a structure directing agent ("SDA") and uses for SSZ-74.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a family of crystalline molecular sieves with unique properties, referred to herein as "molecular sieve SS-74" or simply "SSZ-74".

In accordance with the present invention there is provided a process for converting hydrocarbons comprising contacting a hydrocarbonaceous feed at hydrocarbon converting conditions with a catalyst comprising a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II. The molecular sieve may be predominantly in the hydrogen form. It may also be substantially free of acidity.

Further provided by the present invention is a hydrocracking process comprising contacting a hydrocarbon feedstock under hydrocracking conditions with a catalyst comprising the molecular sieve of this invention, preferably predominantly in the hydrogen form.

This invention also includes a dewaxing process comprising contacting a hydrocarbon feedstock under dewaxing conditions with a catalyst comprising the molecular sieve of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the molecular sieve of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising the molecular sieve of this invention. The molecular sieve may be predominantly in the hydrogen form. The catalyst may contain at least one Group VIII metal.

In accordance with this invention, there is also provided a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) with a catalyst comprising the molecular sieve of this invention, preferably predominantly in the hydrogen form. The catalyst may contain at least one Group VIII metal. The catalyst may be a layered catalyst comprising a first layer comprising the molecular sieve of this invention, and a second layer comprising an aluminosilicate zeolite which is more shape selective than the molecular sieve of said first layer. The first layer may contain at least one Group VIII metal.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. (204° C.) and at a pressure of from about 15 psig to about 3000 psig (0.103-20.7 Mpa gauge) in the presence of added hydrogen gas with a catalyst comprising the molecular sieve of this invention. The molecular sieve may be predominantly in the hydrogen form. The catalyst may contain at least one Group VIII metal.

Further included in this invention is a process for isomerization dewaxing a raffinate comprising contacting said raffinate in the presence of added hydrogen with a catalyst comprising the molecular sieve of this invention. The raffinate may be bright stock, and the molecular sieve may be predominantly in the hydrogen form. The catalyst may contain at least one Group VIII metal.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the molecular sieve of this invention made substantially free of acidity by neutralizing said molecular sieve with a basic metal. Also provided in this invention is such a process wherein the molecular sieve contains a Group VIII metal component.

Also provided by the present invention is a catalytic cracking process comprising contacting a hydrocarbon feedstock in a reaction zone under catalytic cracking conditions in the absence of added hydrogen with a catalyst comprising the molecular sieve of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the molecular sieve of this invention, preferably predominantly in the hydrogen form. The molecular sieve may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the molecular sieve of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives, dimethylnaphthalene or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the molecular sieve of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbons may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the molecular sieve of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the molecular sieve of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the molecular sieve of this invention.

The present invention further provides a process for oligomerizing olefins comprising contacting an olefin feed under oligomerization conditions with a catalyst comprising the molecular sieve of this invention.

This invention also provides a process for converting oxygenated hydrocarbons comprising contacting said oxygenated hydrocarbon with a catalyst comprising the molecular sieve of this invention under conditions to produce liquid products. The oxygenated hydrocarbon may be a lower alcohol.

Further provided in accordance with the present invention is a process for the production of higher molecular weight hydrocarbons from lower molecular weight hydrocarbons comprising the steps of:
(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
(b) withdrawing from said reaction zone a higher molecular weight hydrocarbon containing stream.

The present invention further provides a process for hydrogenating a hydrocarbon feed containing unsaturated hydrocarbons, the process comprising contacting the feed and hydrogen under conditions which cause hydrogenation with a catalyst comprising the molecular sieve of this invention. The catalyst can also contain metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

The present invention also provides a catalyst composition for promoting polymerization of 1-olefins, said composition comprising
(A) a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II; and
(B) an organotitanium or organochromium compound, Also provided is a process for polymerizing 1-olefins, which process comprises contacting 1-olefin monomer with a catalytically effective amount of a catalyst composition comprising
(A) a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II; and
(B) an organotitanium or organochromium compound.

under polymerization conditions which include a temperature and pressure suitable for initiating and promoting the polymerization reaction. The 1-olefin may be ethylene.

In accordance with this invention, there is also provided a process for hydrotreating a hydrocarbon feedstock comprising contacting the feedstock with a hydrotreating catalyst and hydrogen under hydrotreating conditions, wherein the catalyst comprises the molecular sieve of this invention.

DETAILED DESCRIPTION OF THE INVENTION

Figure 1:
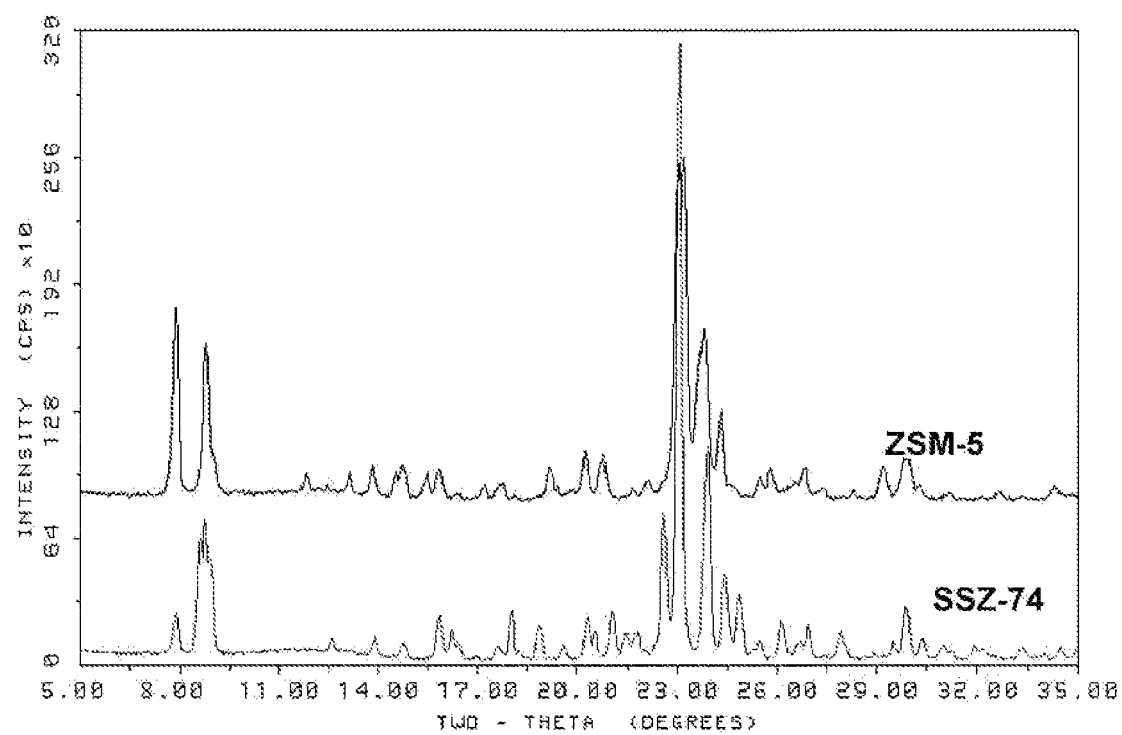
FIG. 1 shows a comparison of two X-ray diffraction patterns, the top one being ZSM-5 and the bottom one being SSZ-74.

The present invention comprises a molecular sieve designated herein "molecular sieve SSZ-74" or simply "SSZ-74".

In preparing SSZ-74, a hexamethylene-1,6-bis-(N-methyl-N-pyrrolidinium) dication is used as a structure directing agent ("SDA"), also known as a crystallization template. The SDA useful for making SSZ-74 has the following structure:

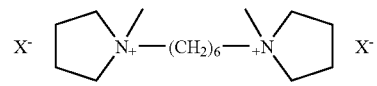

Hexamethylene-1, 6-bis-(N-methyl-N-pyrrolidinium) dication

The SDA dication is associated with anions ($X^-$) which may be any anion that is not detrimental to the formation of the SSZ-74. Representative anions include halogen, e.g., fluoride, chloride, bromide and iodide, hydroxide, acetate, sulfate, tetrafluoroborate, carboxylate, and the like. Hydroxide is the most preferred anion. The structure directing agent (SDA) may be used to provide hydroxide ion. Thus, it is beneficial to ion exchange, for example, a halide to hydroxide ion.

In general, SSZ-74 is prepared by contacting (1) an active sourced(s) of silicon oxide, and, optionally, (2) an active source(s) of aluminum oxide, gallium oxide, iron oxide, boron oxide, titanium oxide, indium oxide and mixtures thereof with the hexamethylene-1,6-bis-(N-methyl-N-pyrrolidinium) dication SDA in the presence of fluoride ion.

SSZ-74 is prepared from a reaction mixture comprising, in terms of mole ratios, the following:

TABLE A

| | Reaction Mixture | |
|---|---|---|
| | Typical | Preferred |
| $SiO_2/X_aO_b$ | 100 and greater | |
| $OH^-/SiO_2$ | 0.20-0.80 | 0.40-0.60 |
| $Q/SiO_2$ | 0.20-0.80 | 0.40-0.60 |
| $M_{2/n}/SiO_2$ | 0-0.04 | 0-0.025 |
| $H_2O/SiO_2$ | 2-10 | 3-7 |
| $HF/SiO_2$ | 0.20-0.80 | 0.30-0.60 | where X is aluminum, gallium, iron, boron, titanium, indium and mixtures thereof, a is 1 or 2, b is 2 when a is 1 (i.e., W is tetravalent); b is 3 when a is 2 (i.e., W is trivalent), M is an alkali metal cation, alkaline earth metal cation or mixtures thereof; n is the valence of M (i.e., 1 or 2); Q is a hexamethylene-1,6-bis-(N-methyl-N-pyrrolidinium) dication and F is fluoride.

As noted above, the $SiO_2/X_aO_b$ mole ratio in the reaction mixture is 100 and greater. This means that the $SiO_2/X_aO_b$ mole ratio can be infinity, i.e. there is no $X_aO_b$ in the reaction mixture. This results in a version of SSZ-74 that is essentially all silica. As used herein, "essentially all silicon oxide" or "essentially all-silica" means that the molecular sieve's crystal structure is comprised of only silicon oxide or is comprised of silicon oxide and only trace amounts of other oxides, such as aluminum oxide, which may be introduced as impurities in the source of silicon oxide.

A preferred source of silicon oxide is tetraethyl orthosilicate. A preferred source of aluminum oxide is LZ-210 zeolite (a type of Y zeolite).

In practice, SSZ-74 is prepared by a process comprising:
(a) preparing an aqueous solution containing (1) a source(s) of silicon oxide, (2) a source(s) of aluminum oxide, gallium oxide, iron oxide, boron oxide, titanium oxide, indium oxide and mixtures thereof, (3) a source of fluoride ion and (4) a hexamethylene-1,6-bis-(N-methyl-N-pyrrolidinium) dication having an anionic counterion which is not detrimental to the formation of SSZ-74;
(b) maintaining the aqueous solution under conditions sufficient to form crystals of SSZ-74; and
(c) recovering the crystals of SSZ-74.

The reaction mixture is maintained at an elevated temperature until the crystals of the SSZ-74 are formed. The hydrothermal crystallization is usually conducted under autogenous pressure, at a temperature between 100° C. and 200° C., preferably between 135° C. and 180° C. The crystallization period is typically greater than 1 day and preferably from about 3 days to about is 20 days. The molecular sieve may be prepared using mild stirring or agitation.

During the hydrothermal crystallization step, the SSZ-74 crystals can be allowed to nucleate spontaneously from the reaction mixture. The use of SSZ-74 crystals as seed material can be advantageous in decreasing the time necessary for complete crystallization to occurs. In addition, seeding can lead to an increased purity of the product obtained by promoting the nucleation and/or formation of SSZ-74 over any undesired phases. When used as seeds, SSZ-74 crystals are added in an amount between 0.1 and 10% of the weight of the first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-74 crystals. The drying step can be performed at atmospheric pressure or under vacuum.

SSZ-74 as prepared has the X-ray diffraction lines of Table I below. SSZ-74 has a composition, as synthesized (i.e., prior to removal of the SDA from the SSZ-74) and in the anhydrous state, comprising the following (in terms of mole ratios):

| | |
|---|---|
| $SiO_2/X_cO_d$ | greater than 100 |
| $M_{2/n}/SiO_2$ | 0-0.03 |
| $Q/SiO_2$ | 0.30-0.70 |
| $F/SiO_2$ | 0.30-0.70 | wherein X is aluminum, gallium, iron, boron, titanium, indium and mixtures thereof, c is 1 or 2; d is 2 when c is 1 (i.e., W is tetravalent) or d is 3 or 5 when c is 2 (i.e., d is 3 when W is trivalent or 5 when W is pentavalent), M is an alkali metal cation, alkaline earth metal cation or mixtures thereof; n is the valence of M (i.e., 1 or 2); Q is a hexamethylene-1,6-bis-(N-methyl-N-pyrrolidinium) dication and F is fluoride.

SSZ-74 is characterized by its X-ray diffraction pattern. SSZ-74, as-synthesized, has a crystalline structure whose X-ray powder diffraction pattern exhibits the characteristic lines shown in Table I.

TABLE I

As-Synthesized SSZ-74

| 2 Theta[a] | d-spacing(Angstroms) | Relative Integrated Intensity (%)[b] |
|---|---|---|
| 7.95 | 11.11 | W |
| 8.68 | 10.18 | M |
| 8.85 | 9.98 | W-M |
| 9.02 | 9.80 | W |
| 22.69 | 3.92 | W-M |
| 23.14 | 3.84 | VS |
| 24.01 | 3.70 | M |
| 24.52 | 3.63 | W |
| 24.93 | 3.57 | W |
| 29.95 | 2.98 | W |

[a] ±0.1
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-74 including actual relative intensities.

TABLE IA

As-Synthesized SSZ-74

| 2 Theta[a] | d-spacing (Angstroms) | Intensity |
|---|---|---|
| 7.95 | 11.11 | 7.9 |
| 8.68 | 10.18 | 21.1 |

TABLE IA-continued

As-Synthesized SSZ-74

| 2 Theta[a] | d-spacing (Angstroms) | Intensity |
|---|---|---|
| 8.85 | 9.98 | 18.7 |
| 9.02 | 9.80 | 11.3 |
| 11.30 | 7.82 | 0.4 |
| 12.70 | 6.96 | 1.8 |
| 13.98 | 6.33 | 2.4 |
| 14.77 | 5.99 | 0.5 |
| 14.85 | 5.96 | 2.1 |
| 15.93 | 5.56 | 6.3 |
| 16.30 | 5.43 | 4.6 |
| 16.50 | 5.37 | 1.8 |
| 17.05 | 5.20 | 0.8 |
| 17.41 | 5.09 | 0.1 |
| 17.71 | 5.00 | 2.0 |
| 18.09 | 4.90 | 7.4 |
| 18.38 | 4.82 | 0.7 |
| 18.89 | 4.69 | 0.9 |
| 18.96 | 4.68 | 4.4 |
| 19.69 | 4.51 | 1.8 |
| 20.39 | 4.35 | 5.1 |
| 20.63 | 4.30 | 4.2 |
| 21.12 | 4.20 | 7.7 |
| 21.55 | 4.12 | 5.4 |
| 21.75 | 4.08 | 0.5 |
| 21.80 | 4.07 | 1.4 |
| 21.88 | 4.06 | 2.1 |
| 21.96 | 4.04 | 1.5 |
| 22.17 | 4.01 | 0.8 |
| 22.69 | 3.92 | 18.9 |
| 23.14 | 3.84 | 100.0 |
| 23.89 | 3.72 | 9.4 |
| 24.01 | 3.70 | 25.6 |
| 24.52 | 3.63 | 13.7 |
| 24.68 | 3.60 | 2.1 |
| 24.93 | 3.57 | 11.3 |
| 25.09 | 3.55 | 0.9 |
| 25.37 | 3.51 | 1.7 |
| 25.57 | 3.48 | 2.7 |
| 26.20 | 3.40 | 5.5 |
| 26.31 | 3.38 | 0.8 |
| 26.67 | 3.34 | 2.0 |
| 26.76 | 3.33 | 1.0 |
| 26.82 | 3.32 | 0.9 |
| 27.01 | 3.30 | 3.4 |
| 27.05 | 3.29 | 0.8 |
| 27.48 | 3.24 | 0.8 |
| 27.99 | 3.19 | 4.2 |
| 28.18 | 3.16 | 0.8 |
| 28.78 | 3.10 | 0.6 |
| 29.03 | 3.07 | 0.7 |
| 29.31 | 3.04 | 0.9 |
| 29.58 | 3.02 | 2.4 |
| 29.95 | 2.98 | 9.6 |
| 30.44 | 2.93 | 3.7 |
| 31.09 | 2.87 | 3.1 |
| 31.36 | 2.85 | 0.8 |
| 31.98 | 2.80 | 2.2 |
| 32.23 | 2.78 | 1.7 |
| 32.37 | 2.76 | 0.6 |
| 32.64 | 2.74 | 1.5 |
| 33.03 | 2.71 | 0.1 |
| 33.34 | 2.69 | 1.0 |
| 33.47 | 2.68 | 1.3 |
| 34.08 | 2.63 | 0.7 |
| 34.55 | 2.59 | 1.8 |
| 34.73 | 2.58 | 0.4 |

[a] ±0.1

After calcination, the X-ray powder diffraction pattern for SSZ-74 exhibits the characteristic lines shown in Table II below.

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M |

[a] ±0.1

Table IIA below shows the X-ray powder diffraction lines for calcined SSZ-74 including actual relative intensities.

TABLE IIA

Calcined SSZ-74

| 2 Theta[a] | d-spacing (Angstroms) | Relative Integrated Intensity (%) |
|---|---|---|
| 7.98 | 11.07 | 34.9 |
| 8.70 | 10.16 | 86.8 |
| 8.89 | 9.93 | 40.2 |
| 9.08 | 9.74 | 47.0 |
| 9.66 | 9.15 | 1.0 |
| 11.26 | 7.85 | 0.4 |
| 11.34 | 7.80 | 0.5 |
| 12.76 | 6.93 | 1.1 |
| 13.26 | 6.67 | 4.6 |
| 14.02 | 6.31 | 13.4 |
| 14.93 | 5.93 | 20.9 |
| 16.03 | 5.52 | 23.5 |
| 16.39 | 5.40 | 4.3 |
| 16.61 | 5.33 | 4.4 |
| 17.12 | 5.18 | 3.0 |
| 17.80 | 4.98 | 2.8 |
| 18.19 | 4.87 | 7.6 |
| 19.05 | 4.66 | 1.9 |
| 19.74 | 4.49 | 0.4 |
| 20.44 | 4.34 | 3.0 |
| 20.75 | 4.28 | 3.4 |
| 21.19 | 4.19 | 7.7 |
| 21.67 | 4.10 | 4.1 |
| 21.99 | 4.04 | 5.8 |
| 22.68 | 3.92 | 3.7 |
| 22.79 | 3.90 | 9.5 |
| 23.26 | 3.82 | 100.0 |
| 23.95 | 3.71 | 14.2 |

[a] ±0.1

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

Representative peaks from the X-ray diffraction pattern of calcined SSZ-74 are shown in Table II. Calcination can result in changes in the intensities of the peaks as compared to patterns of the "as-made" material, as well as minor shifts in the diffraction pattern.

Crystalline SSZ-74 can be used as-synthesized, but preferably will be thermally treated (calcined). Usually, it is desirable to re-move the alkali metal cation (if any) by ion exchange and replace it with hydrogen, ammonium, or any desired metal ion.

SSZ-74 can be formed into a wide variety of physical shapes. Generally speaking, the molecular sieve can be in the form of a powder, a granule, or a molded products such as extrudate having a particle size sufficient to pass through a 2-mesh (Tyler) screen and be retained on a 400-mesh (Tyler) screen. In cases where the catalyst is molded, such as by extrusion with an organic binder, the SSZ-74 can be extruded before drying, or, dried or partially dried and then extruded.

SSZ-74 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-74 molecular sieves are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-74 is expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes polymerizing and oligomerizing olefinic or acetylenic compounds such as isobutylene and butene-1, polymerization of 1-olefins (e.g., ethylene), reforming, isomerizing polyalkyl substituted, aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading).

The SSZ-74 catalysts may have high selectivity, and under hydrocarbon conversion conditions can provide a high percentage of desired products relative to total products.

For high catalytic activity, the SSZ-74 molecular sieve should be predominantly in its hydrogen ion form. Generally, the molecular sieve is converted to its hydrogen form by ammonium exchange followed by calcination. If the molecular sieve is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

SSZ-74 molecular sieves can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks. Other feeds include synthetic feeds, such as those derived from a Fischer Tropsch process, including an oxygenate-containing Fischer Tropsch process boiling below about 371° C. (700° F.). In general, the feed can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feed stock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-74 in the hydrocarbon conversion reactions of this invention. Preferred conditions are indicated in parentheses.

| Process | Temp., ° C. | Pressure | LHSV |
|---|---|---|---|
| Hydrocracking | 175-485 | 0.5-350 bar | 0.1-30 |
| Dewaxing | 200-475 (250-450) | 15-3000 psig, 0.103-20.7 Mpa gauge (200-3000, 1.38-20.7 Mpa gauge) | 0.1-20 (0.2-10) |
| Aromatics formation | 400-600 (480-550) | atm.~10 bar | 0.1-15 |
| Cat. Cracking | 127~885 | subatm.~$^1$ (atm.-5 atm.) | 0.5~50 |
| Oligomerization | 232~649$^2$ 10-232$^4$ (27-204)$^4$ | 0.1~50 atm.$^{2,3}$ — — | 0.2~50$^2$ 0.05~20$^5$ (0.1-10)$^5$ |
| Paraffins to aromatics | 100-700 | 0-1000 psig | 0.5-40$^5$ |
| Condensation of alcohols | 260-538 | 0.5-1000 psig, 0.00345-6.89 Mpa gauge | 0.5-50$^5$ |
| Isomerization | 93-538 (204~315) | 50-1000 psig, 0.345~6.89 Mpa gauge | 1-10 (1~4) |
| Xylene isomerization | 260-593$^2$ (315-566)$^2$ 38-371$^4$ | 0.5-50 atm.$^2$ (1~5 atm)$^2$ 1~200 atm.$^4$ | 0.1-100$^5$ (0.5-50)$^5$ 0.5-50 |

$^1$Several hundred atmospheres
$^2$Gas phase reaction
$^3$Hydrocarbon partial pressure
$^4$Liquid phase reaction
$^5$WHSV Other reaction conditions and parameters are provided below.

Hydrocracking

Using a catalyst which comprises SSZ-74, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-74, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-74 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 300,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the produce and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15-3000 psi (0.103-20.7 Mpa) with a catalyst comprising SSZ-74 and at least one Group VIII metal.

The SSZ-74 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalysts preferably in the range of from about 0.05 to 5% by weight. The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-74 may also be utilized as a dewaxing catalyst in the form of a layered catalyst. That is, the catalyst comprises a first layer comprising molecular sieve SSZ-74 and at least one Group VIII metal, and a second layer comprising an aluminosilicate zeolite which is more shape selective than molecular sieve SSZ-74. The use of layered catalysts is disclosed in U.S. Pat. No. 5,149,421, issued Sep. 22, 1992 to Miller, which is incorporated by reference herein in its entirety. The layering may also include a bed of SSZ-74 layered with a non-zeolitic component designed for either hydrocracking or hydrofinishing.

SSZ-74 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 Mpa gauge) at space velocities (LHSV) between about 0.1 and 20 and a hydrogen recycle rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-74. For example, a $C_{20+}$ lube oil may be made by isomerizing a $C_{20+}$ olefin feed over a catalyst comprising SSZ-74 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at, a temperature of at least about 400° F. (204° C.) and at a pressure of from about 15 psig to about 3000 psig (0.103-20.7 Mpa gauge) in the presence of added hydrogen gas with a catalyst comprising SSZ-74 in the hydrogen form and at least one Group VIII metal.

Aromatics Formation

SSZ-74 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-74. It is also possible to convert heavier feeds into BTX or naphthalene derivatives of value using a catalyst comprising SSZ-74.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the molecular sieve with a basic metal, e.g. alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The molecular sieve itself can be substantially free of acidity only at very high silica:alumina mole ratios.

Catalytic Cracking

Hydrocarbon cracking stocks can be catalytically cracked in the absence of hydrogen using SSZ-74, preferably predominantly in the hydrogen form.

When SSZ-74 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the SSZ-74 is generally between about 1:10 and about 500:1, desirably between about: 1:10 and about 200:1, preferably between about 1:2 and about 50:1, and most preferably is between about 1:1 and about 20:1. The novel molecular sieve and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-74 in the hydrogen form, with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.). Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-74 can be used in a process for the alkylation of transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-74.

SSZ-74 can also be used for removing benzene from gasoline by alkylating the benzene as described above and removing the alkylated product from the gasoline.

For high catalytic activity, the SSZ-74 molecular sieve should be predominantly in its hydrogen ion form. It is preferred that, after calcination, at least 80% of the cation sites are occupied by hydrogen ions and/or rare earth ions.

Examples of suitable aromatic hydrocarbon feedstocks which may be it alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethyl benzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 Mpa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 Mpa gauge), preferably 300 psig to 600 psig (2.07 to 4.14 Mpa gauge). The weight hourly space velocity will range from about 0.1 to 10. U.S. Pat. No. 5,082,990 issued on Jan. 21, 1992 to Hsieh, et al. describes such processes and is incorporated herein by reference.

Conversion of Paraffins to Aromatics

SSZ-74 can be used to convert light gas $C_2$-$C_6$ paraffins to higher molecular weight hydrocarbons including aromatic compounds. Preferably, the molecular sieve will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

SSZ-74 can be used to isomerize olefins. The feed stream is a hydrocarbon stream containing at least one $C_{4-6}$ olefin, preferably a $C_{4-6}$ normal olefin, more preferably normal butane. Normal butene as used in this specification means all forms of normal butene, e.g., 1-butene, cis-2 butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40-60 weight percent normal butenes. A methyl-tert-butyl ether unit effluent typically contains 40-100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-74. The process may be carried out generally at a temperature from about 625° F. to about 950° F. (329-510° C.), for butenes, preferably from about 700° F. to about 900° F. (371-482° C.), and about 350° F. to about 650° F. (177-343° C.) for pentenes and hexenes. The pressure ranges from subatmospheric to about 200 psig (1.38 Mpa gauge), preferably from about psig to about 200 psig (0.103 to 1.38 Mpa gauge), and more preferably from about 1 psig to about 150 psig (0.00689 to 1.03 Mpa gauge).

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

SSZ-74 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, pad of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such as toluene, trimethylbenzene, naphthenes or paraffins.

Oligomerization

It is expected that SSZ-74 can also be used to oligomerize straight and branched chain olefins having from about 2 to 21 and preferably 2-5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-74.

The molecular sieve can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the molecular sieve have a fairly low aromatization activity, i.e., in which the amount of aromatics produced is not more than about 20% by weight. This is accomplished by using a molecular sieve with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such molecular sieves may be obtained by steaming, by use in a conversion process or by any other method which may occur to one skilled in this art.

Condensation of Alcohols

SSZ-74 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-74 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

Polymerization of 1-Olefins

The molecular sieve of the present invention may be used in a catalyst for the polymerization of 1-olefins, e.g., the polymerization of ethylene. To form the olefin polymerization catalyst, the molecular sieve as hereinbefore described is reacted with a particular type of organometallic compound. Organometallic compounds, useful in forming the polymerization catalyst include trivalent and tetravalent organotitanium and organochromium compounds having alkyl moieties and, optionally, halo moieties. In the context of the present invention the term "alkyl" includes both straight and branched chain alkyl, cycloalkyl and alkaryl groups such as benzyl.

Examples of trivalent and tetravalent organochromium and organotitanium compounds are disclosed in U.S. Pat. No. 4,376,722, issued Mar. 15, 1983 to Chester et al., U.S. Pat. No. 4,377,497, issued Mar. 22, 1983 to Chester et al., U.S. Pat. No. 4,446,243, issued May 1, 1984 to Chester et al., and U.S. Pat. No. 4,526,942, issued Jul. 2, 1985 to Chester et al. The disclosure of the aforementioned patents are incorporated herein by reference in their entirety.

Examples of the organometallic compounds used to form the polymerization catalyst include, but are not limited to, compounds corresponding to the general formula:

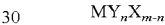

$$MY_nX_{m-n}$$

wherein M is a metal selected from titanium and chromium; Y is alkyl; X is halogen (e.g., Cl or Br); n is 1-4; and m is greater than or equal to n and is 3 or 4.

Examples of organotitanium and organochromium compounds encompassed by such a formula include compounds of the formula $CrY_4$, $CrY_3$, $CrY_3X$, $CrY_2X$, $CrY_2X_2$, $CrYX_2$, $CrYX_3$, $TiY_4$, $TiY_3$, $TiY_3X$, $TiY_2X$, $TiY_2X_2$, $TiYX_2$, $TiYX_3$, wherein X can be Cl or Br and Y can be methyl, ethyl, propyl, isopropyl, butyl, isobutyl, sec-butyl, tert-butyl, pentyl, isopentyl, neopentyl, hexyl, isohexyl, neohexyl, 2-ethybutyl, octyl, 2-ethylhexyl, 2,2-diethylbutyl, 2-isopropyl-3-methylbutyl, etc., cyclohexylalkyls such as, for example, cyclohexylmethyl, 2-cyclohexylethyl, 3-cyclohexylpropyl, 4-cyclohexylbutyl, and the corresponding alkyl-substituted cyclohexyl radicals as, for example, (4-methylcyclohexyl) methyl neophyl, i.e. beta, beta-dimethyl-phenethyl, benzyl, ethylbenzyl, and p-isopropylbenzyl. Preferred examples of Y include $C_{1-5}$ alkyl, especially butyl.

The organotitanium and organochromium materials employed in the catalyst can be prepared by techniques well known in the art. See, for example the aforementioned Chester et al. patents.

The organotitanium or organochromium compounds can be with the molecular sieve of the present invention, such as by reacting the organometallic compound and the molecular sieve, in order to form the olefin polymerization catalyst. Generally, such a reaction takes place in the same reaction medium used to prepare the organometallic compound under conditions which promote formation of such a reaction product. The molecular sieve can simply be added to the reaction mixture after formation of the organometallic compound has been completed. Molecular sieve is added in an amount sufficient to provide from about 0.1 to 10 parts by weight, preferably from about 0.5 to 5 parts by weight, of organometallic compound in the reaction medium per 100 parts by weight of molecular sieve.

Temperature of the reaction medium during reaction of organometallic compound with molecular sieve is also maintained at a level which is low enough to ensure the stability of the organometallic reactant. Thus, temperatures in the range of from about −150° C. to 50° C., preferably from about −80° C., to 0° C., can be usefully employed. Reaction times of from about 0.01 to 10 hours, more preferably from about 0.1 to 1 hour, can be employed in reacting the organotitanium or organochromium compound with the molecular sieve.

Upon completion of the reaction, the catalyst material so formed may be recovered and dried by evaporating the reaction medium solvent under a nitrogen atmosphere. Alternatively, olefin polymerization reactions can be conducted in this same solvent based reaction medium used to form the catalyst.

The polymerization catalyst can be used to catalyze polymerization of 1-olefins. The polymers produced using the catalysts of this invention are normally solid polymers of at least one mono-1-olefin containing from 2 to 8 carbon atoms per molecule. These polymers are normally solid homopolymers of ethylene or copolymers of ethylene with another mono-1-olefin containing 3 to 8 carbon atoms per molecule. Exemplary copolymers include those of ethylene/propylene, ethylene/1-butene, ethylene/1-hexene, and ethylene/1-octene and the like. The major portion of such copolymers is derived from ethylene and generally consists of about 80-99, preferably 95-99 mole percent of ethylene. These polymers are well suited for extrusion, blow molding, injection molding and the like.

The polymerization reaction can be conducted by contacting monomer or monomers, e.g., ethylene, alone or with one or more other olefins, and in the substantial absence of catalyst poisons such as moisture and air, with a catalytic amount of the supported organometallic catalyst at a temperature and at a pressure sufficient to initiate the polymerization reaction. If desired, an inert organic solvent may be used as a diluent and to facilitate materials handling if the polymerization reaction is conducted with the reactants in the liquid phase, e.g. in a particle form (slurry) or solution process. The reaction may also be conducted with reactants in the vapor phase, e.g., in a fluidized bed arrangement in the absence of a solvent but, if desired, in the presence of an inert gas such as nitrogen.

The polymerization reaction is carried out at temperatures of from about 30° C. or less, up to about 200° C. or more, depending to a great extent on the operating pressure, the pressure of the olefin monomers, and the particular catalyst being used and its concentration. Naturally, the selected operating temperature is also dependent upon the desired polymer melt index since temperature is definitely a factor in adjusting the molecular weight of the polymer. Preferably, the temperature used is from about 30° C. to about 100° C. in a conventional slurry or "particle forming" process or from 100° C. to 150° C. in a "solution forming" process. A temperature of from about 70° C. to 110° C. can be employed for fluidized bed processes.

The pressure to be used in the polymerization reactions can be any pressure sufficient to initiate the polymerization of the monomer(s) to high molecular weight polymer. The pressure, therefore, can range from subatmospheric pressures, using an inert gas as diluent, to superatmospheric pressures of up to about 30,000 psig or more. The preferred pressure is from atmospheric (0 psig) up to about 1000 psig. As a general rule, a pressure of 20 to 800 psig is most preferred.

The selection of an inert organic solvent medium to be employed in the solution or slurry process embodiments of this invention is not too critical, but the solvent should be inert to the supported organometallic catalyst and olefin polymer produced, and be stable at the reaction temperature used. It is not necessary, however, that the inert organic solvent medium also serve as a solvent for the polymer to be produced. Among the inert organic solvents applicable for such purposes may be mentioned saturated aliphatic hydrocarbons having from about 3 to 12 carbon atoms per molecule such as hexane, heptane, pentane, isooctane, purified kerosene and the like, saturated cycloaliphatic hydrocarbons having from about 5 to 12 carbon atoms per molecule such as cyclohexane, cyclopentane, dimethylcyclopentane and methylcyclohexane and the like and aromatic hydrocarbons having from about 6 to 12 carbon atoms per molecule such as benzene, toluene, xylene, and the like. Particularly preferred solvent media are cyclohexane, pentane, hexane and heptane.

Hydrogen can be introduced into the polymerization reaction zone in order to decrease the molecular weight of the polymers produced (i.e., give a much higher Melt Index, MI). Partial pressure of hydrogen when hydrogen is used can be within the range of 5 to 100 psig, preferably 25 to 75 psig. The melt indices of the polymers produced in accordance with the instant invention can range from about 0.1 to about 70 or even higher.

More detailed description of suitable polymerization conditions including examples of particle form, solution and fluidized bed polymerizations arrangements are found in Karapinka; U.S. Pat. No. 3,709,853; Issued Jan. 9, 1973 and Karol et al; U.S. Pat. No. 4,086,408; Issued Apr. 25, 1978. Both of these patents are incorporated herein by reference.

Hydrotreating

SSZ-74 is useful in a hydrotreating catalyst. During hydrotreatment, oxygen, sulfur and nitrogen present in the hydrocarbonaceous feed is reduced to low levels. Aromatics and olefins, if present in the feed, may also have their double bonds saturated. In some cases, the hydrotreating catalyst and hydrotreating conditions are selected to minimize cracking reactions, which can reduce the yield of the most desulfided product (typically useful as a fuel).

Hydrotreating conditions typically include a reaction temperature between 400-900° F. (204-482° C.), preferably 650-850° F. (343-454° C.); a pressure between 500 and 5000 psig (3.5-34.6 Mpa), preferably 1000 to 3000 psig (7.0-20.8 MPa); a feed rate (LHSV) of 0.5 $hr^{-1}$ to 20 $hr^{-1}$ (v/v); and overall hydrogen consumption 300 to 2000 scf per barrel of liquid hydrocarbon feed (53.4-356 $m^3H_2/m^3$ feed). The hydrotreating catalyst will typically be a composite of a Group VI metal or compound thereof, and a Group VIII metal or compound thereof supported on the molecular sieve of this invention. Typically, such hydrotreating catalyst are presulfided.

Catalysts useful for hydrotreating hydrocarbon feeds are disclosed in U.S. Pat. No. 4,347,121, issued Aug. 31, 1982 to Mayer et al, and U.S. Pat. No. 4,810,357 issued Mar. 7, 1989 to Chester et al, both of which are incorporated herein by reference in their entirety. Suitable catalysts include noble metals from Group VIII, such as Fe, Co, Ni, Pt or Pd, and/or Group VI metals, such as Cr, Mo, Sn or W. Examples of combinations of Group VIII and Group VI metals include Ni—Mo or Ni—Sn. Other suitable catalysts are described in U.S. Pat. No. 4,157,294, issued Jun. 5, 1979 to Iwao et al, and U.S. Pat. No. 3,904,513, issued Sep. 9, 1975 to Fischer et al. U.S. Pat. No. 3,852,207, issued Dec. 3, 1974 to Strangeland et al, describes suitable noble metal catalysts and mild hydrotreating conditions. The contents of these patents are hereby incorporated by reference.

The amount of hydrogenation component(s) in the catalyst suitably range from about 0.5% to about 10% by weight of Group VIII component(s) and from 5% to about 25% by weight of Group VI metal component(s), calculated as metal oxide(s) per 100 parts by weight of total catalyst, where the percentages by weight are based on the weight of the catalyst before sulfiding. The hydrogenation component(s) in the catalyst may be in the oxidic and/or sulfidic form.

Hydrogenation

SSZ-74 can be used in a catalyst to catalyze hydrogenation of a hydrocarbon feed containing unsaturated hydrocarbons. The unsaturated hydrocarbons can comprise olefins, dienes, polyenes, aromatic compounds and the like.

Hydrogenation is accomplished by contacting the hydrocarbon feed containing unsaturated hydrocarbons with hydrogen in the presence of a catalyst comprising SSZ-74. The catalyst can also contain one or more metals of Group VIB and Group VIII, including salts, complexes and solutions thereof. Reference to these catalytically active metals is intended to encompass such metals or metals in the elemental state or in some form such as an oxide, sulfide, halide, carboxylate and the like. Examples of such metals include metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

The hydrogenation component of the catalyst (i.e., the aforementioned metal) is present in an amount effective to provide the hydrogenation function of the catalyst, preferably in the range of from 0.05 to 25% by weight.

Hydrogenation conditions, such as temperature, pressure, space velocities, contact time and the like are well known in the art.

EXAMPLES

The following examples demonstrate but do not limit the present invention.

Example 1

Synthesis of Hexamethylene-1,6-bis-(N-methyl-N-pyrrolidinium) dication SDA

In 50 ml of acetone was dissolved 5 ml (48 mmoles) of N-methyl pyrrolidine. 4.9 Grams of 1,6 dibromohexane (20 mmoles) were added and the resulting mixture was stirred at room temperature for three days. Solids formed and were collected by filtration and washed with ether and kept in a vacuum oven. Then 3.71 grams of the dried solid was mixed into 18.7 grams of water and 9.57 grams of AG1-X8 resin for exchange to the OH form. The exchange was run overnight and then the solution was collected and titrated.

Example 2

Synthesis of All-Silica SSZ-74

6.4 Grams of the solution from Example 1 (3 mmoles) was mixed in a tared Teflon cup with 1.26 grams of tetraethyl orthosilicate and then allowed to evaporate (in a hood) for several days as hydrolysis occurred. A second reaction was set up the same way. After evaporation to the appearance of dryness, one reaction was given 0.20 gram of water and mixed. The second was given 0.60 gram of water and the same treatment ensued. 0.125 Gram of about 50% HF was carefully added to each reaction mixture and the contents were stirred with a plastic spatula and a thick gel formed. In the first case the H2O/SiO2 ratio was now roughly 3.5 and it was 7.0 in the second case. The materials were heated to 150° C. and at 43 RPM in tumbled Parr reactors placed in a Blue M convection heating oven. The reactions were cooled and opened in 6 day periods with a small amount examined by Scanning Electron Microscopy to determine if crystals had formed. After 22 days there was crystalline material in both and the solids were collected (filtration) and washed with copious amounts of water, air dried and then examined by X-ray diffraction (XRD). The product in both cases was SSZ-74.

Example 3

Calcination of SSZ-74

The products from both reactions in Example 2 were calcined in stages and in air to 595° C. to remove the organic content. The materials were found to be stable and the XRD patterns showed the relationship to the as-made SSZ-74.

Example 4

Adsorption of 2,2-Dimethylbutane

The calcined material of Example 3 was then tested for the uptake of the hydrocarbon 2,2-dimethylbutane. This adsorbate does not enter small pore zeolites (8-ring portals) and sometimes is hindered in entering intermediate pore zeolites like ZSM-5. The SSZ-74 showed a profile more characteristic of intermediate pore materials (as contrasted to Y zeolite, a large pore material), showing steady gradual uptake of the adsorbate.

SSZ-74 was shown to adsorb about 0.08 cc/gram after 3 hours of exposure to the 2,2 dimethyl butane adsorbate using a pulsed mode. This value compares with an analysis for ZSM-5 zeolite which gives a value closer to 0.07 cc/gm at the same point in time under the same experimental conditions. This would indicate that the pores of SSZ-74 are at least 10-rings Example 5

Synthesis of Aluminosilicate SSZ-74

The synthesis parameters of Example 2 were repeated except for the following changes. (1) 0.04 gram of Y zeolite material LZ-210 was added as a potential contributor of Al; (2) the initial H2O/SiO2 ratio for the synthesis was adjusted to 5; (3) seeds of a successful SSZ-74 product were added; and (4) the reaction was run at 170° C. After 9 days there was crystalline material which was SSZ-74 when worked up and analyzed by XRD. The solids were calcined then as in Example 3.

Example 6

Constraint Index 0.12 grams of the material from Example 5 in a 20-40 pelleted and meshed range, was loaded into a stainless steel reactor and run in a Constraint Index test (50/50 n-hexane/3-methylpentane). The normal feed rate was used (8 µl/min.) and the test was run at 700° F. after the catalyst had been dried in the reactor to near 1000° F. Helium flow was used. At 10 minutes on-stream nearly 30% of the feed was being converted with about equal amounts of each reactant. The selectivity did not change as the catalyst fouled to half the conversion at 100 minutes. The pores of the active SSZ-74 were at least intermediate in size.

Example 7

Synthesis of Aluminosilicate SSZ-74

Three mMoles of SDA solution and 1.26 grams (6 mMoles) of tetraethylorthosilicate were combined in a Teflon cup for a Parr reactor. The contents were allowed to react and then most of the water and then the ethanol by-product were allowed to evaporate in a hood over several days. Once the H2O/SiO2 ratio was about 5, from the evaporation, 0.04 grams of LZ-210 zeolite were added (LZ-210 is a Y zeolite which has been treated with $(NH_4^+)_2SiF_6$ to provide some de-alumination). A few mg of seeds of SSZ-74 were added in the as-made state. Lastly, 0.132 gram of 50% HF was added and the reactor was closed up and heated at 170° C., 43 RPM, for six days. A sample of the cooled reaction product showed nicely crystalline material in an electron microscope. The reaction contents were worked up and dried. Analysis by X-ray diffraction showed the product to be molecular sieve SSZ-74.

The sample was calcined (in air to 595° C.) and then pelleted and meshed (20-40) and ruin in a standard Constraint Index test. At 700° F. the initial conversion was 28% with a CI value of 1.1. With time-on-stream the catalyst showed a steady deactivation while the CI value did not change much.

What is claimed is:

1. A process for converting hydrocarbons comprising contacting a hydrocarbonaceous feed at hydrocarbon converting conditions with a catalyst comprising a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II.

2. The process of claim 1 wherein the molecular sieve has a mole ratio greater than about 15 of (1) silicon oxide to (2) an oxide selected from aluminum oxide, gallium oxide, iron oxide, boron oxide, titanium oxide, indium oxide and mixtures thereof.

3. The process of claim 2 wherein the molecular sieve is predominantly in the hydrogen form.

4. The process of claim 2 wherein the molecular sieve is substantially free of acidity.

5. The process of claim 2 wherein the process is a hydrocracking process comprising contacting the catalyst with a hydrocarbon feedstock under hydrocracking conditions.

6. The process of claim 5 wherein the molecular sieve is predominantly in the hydrogen form.

7. The process of claim 2 wherein the process is a dewaxing process comprising contacting the catalyst with a hydrocarbon feedstock under dewaxing conditions.

8. The process of claim 7 wherein the molecular sieve is predominantly in the hydrogen form.

9. The process of claim 2 wherein the process is a process for improving the viscosity index of a dewaxed product of waxy hydrocarbon feeds comprising contacting the catalyst with a waxy hydrocarbon feed under isomerization dewaxing conditions.

10. The process of claim 9 wherein the molecular sieve is predominantly in the hydrogen form.

11. The process of claim 2 wherein the process is a process for producing a $C_{20+}$ lube oil from a $C_{20+}$ olefin feed comprising isomerizing said olefin feed under isomerization conditions over the catalyst.

12. The process of claim 11 wherein the molecular sieve is predominantly in the hydrogen form.

13. The process of claim 11 wherein the catalyst further comprises at least one Group VIII metal.

14. The process of claim 2 wherein the process is a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) under dewaxing conditions with the catalyst.

15. The process of claim 14 wherein the molecular sieve is predominantly in the hydrogen form.

16. The process of claim 14 wherein the catalyst further comprises at least one Group VIII metal.

17. The process of claim 14 wherein said catalyst comprises a layered catalyst comprising a first layer comprising the molecular sieve and at least one Group VIII metal, and a second layer comprising an aluminosilicate zeolite which is more shape selective than the molecular sieve of said first layer.

18. The process of claim 2 wherein the process is a process for preparing a lubricating oil which comprises:
hydrocracking in a hydrocracking zone a hydrocarbonaceous feedstock to obtain an effluent comprising a hydrocracked oil; and
catalytically dewaxing said effluent comprising hydrocracked oil at a temperature of at least about 400° F. (204° C.) and at a pressure of from about 15 psig to about 3000 psig (0.103 to 20.7 MPa gauge) in the presence of added hydrogen gas with the catalyst.

19. The process of claim 18 wherein the molecular sieve is predominantly in the hydrogen form.

20. The process of claim 18 wherein the catalyst further comprises at least one Group VIII metal.

21. The process of claim 2 wherein the process is a process for isomerization dewaxing a raffinate comprising contacting said raffinate in the presence of added hydrogen under isomerization dewaxing conditions with the catalyst.

22. The process of claim 21 wherein the molecular sieve is predominantly in the hydrogen form.

23. The process of claim 21 wherein the catalyst further comprises at least one Group VIII metal.

24. The process of claim 21 wherein the raffinate is bright stock.

25. The process of claim 2 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

26. The process of claim 25 wherein the molecular sieve is substantially free of acid.

27. The process of claim 25 wherein the molecular sieve contains a Group VIII metal component.

28. The process of claim 2 wherein the process is a catalytic cracking process comprising contacting a hydrocarbon feedstock in a reaction zone under catalytic cracking conditions in the absence of added hydrogen with the catalyst.

29. The process of claim 28 wherein the molecular sieve is predominantly in the hydrogen form.

30. The process of claim 28 wherein the catalyst additionally comprises a large pore crystalline cracking component.

31. The process of claim 2 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

32. The process of claim 31 wherein the molecular sieve is predominantly in the hydrogen form.

33. The process of claim 31 wherein the molecular sieve has been impregnated with at least one Group VIII metal.

34. The process of claim 31 wherein the catalyst has been calcined in a steam/air mixture at an elevated temperature after impregnation of the Group VIII metal.

35. The process of claim 33 wherein the Group VIII metal is platinum.

36. The process of claim 2 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

37. The process of claim 36 wherein the molecular sieve is predominantly in the hydrogen form.

38. The process of claim 36 wherein the olefin is a $C_2$ to $C_4$ olefin.

39. The process of claim 38 wherein the aromatic hydrocarbon and olefin are present in a molar ratio of about 4:1 to about 20:1, respectively.

40. The process of claim 38 wherein the aromatic hydrocarbon is selected from the group consisting of benzene, toluene, ethylbenzene, xylene, naphthalene, naphthalene derivatives, dimethylnaphthalene or mixtures thereof.

41. The process of claim 2 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

42. The process of claim 41 wherein the molecular sieve is predominantly in the hydrogen form.

43. The process of claim 41 wherein the aromatic hydrocarbon and the polyalkyl aromatic hydrocarbon are present in a molar ratio of from about 1:1 to about 25:1, respectively.

44. The process of claim 41 wherein the aromatic hydrocarbon is selected from the group consisting of benzene, toluene, ethylbenzene, xylene, or mixtures thereof.

45. The process of claim 41 wherein the polyalkyl aromatic hydrocarbon is a dialkylbenzene.

46. The process of claim 2 wherein the process is a process to convert paraffins to aromatics which comprises contacting paraffins under conditions which cause paraffins to convert to aromatics with a catalyst comprising the molecular sieve and gallium, zinc, or a compound of gallium or zinc.

47. The process of claim 2 wherein the process is a process for isomerizing olefins comprising contacting said olefin under conditions which cause isomerization of the olefin with the catalyst.

48. The process of claim 2 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

49. The process of claim 2 wherein the process is a process for oligomerizing olefins comprising contacting an olefin feed under oligomerization conditions with the catalyst.

50. A process for converting oxygenated hydrocarbons comprising contacting said oxygenated hydrocarbon under conditions to produce liquid products with a catalyst comprising a molecular sieve having a mole ratio greater than about 15 of an oxide of a first tetravalent element to an oxide of a second tetravalent element which is different from said first tetravalent element, trivalent element, pentavalent element or mixture thereof and having, after calcination, the X-ray diffraction lines of Table II.

51. The process of claim 50 wherein the oxygenated hydrocarbon is a lower alcohol.

52. The process of claim 51 wherein the lower alcohol is methanol.

53. The process of claim 2 wherein the process is a process for the production of higher molecular weight hydrocarbons from lower molecular weight hydrocarbons comprising the steps of:
  (a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
  (b) withdrawing from said reaction zone a higher molecular weight hydrocarbon-containing stream.

54. The process of claim 53 wherein the metal or metal compound comprises a lanthanide or actinide metal or metal compound.

55. The process of claim 53 wherein the lower molecular weight hydrocarbon is methane.

56. The process of claim 2 wherein the process is a process for polymerizing 1-olefins, which process comprises contacting 1-olefin monomer with a catalytically effective amount of a catalyst composition comprising
  (A) a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II; and
  (B) an organotitanium or organochromium compound;
under polymerization conditions which include a temperature and pressure suitable for initiating and promoting the polymerization reaction.

57. The process of claim 56 wherein the 1-olefin monomer is ethylene.

58. The process of claim 2 wherein the process is a process for hydrogenating a hydrocarbon feed containing unsaturated hydrocarbons, the process comprising contacting the feed with hydrogen under conditions which cause hydrogenation with the catalyst.

59. The process of claim 58 wherein the catalyst contains metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

60. A process for hydrotreating a hydrocarbon feedstock comprising contacting the feedstock with a hydrotreating catalyst and hydrogen under hydrotreating conditions, wherein the catalyst comprises a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II.

61. The process of claim 60 wherein the catalyst contains a Group VIII metal or compound, a Group VI metal or compound or combinations thereof.

* * * * *